United States Patent [19]

Horn

[11] Patent Number: 5,039,648
[45] Date of Patent: Aug. 13, 1991

[54] PROCESS FOR THE PREPARATION OF COBALT CATALYSTS

[75] Inventor: Gerhardt Horn, Oberhausen, Fed. Rep. of Germany

[73] Assignee: Hoechst Aktiengesellschaft, Fed. Rep. of Germany

[21] Appl. No.: 291,748

[22] Filed: Dec. 29, 1988

[30] Foreign Application Priority Data

Dec. 30, 1987 [DE] Fed. Rep. of Germany ....... 3744507

[51] Int. Cl.$^5$ .......................... B01J 21/04; B01J 21/06; B01J 23/78; B01J 23/84
[52] U.S. Cl. .................................... 502/260; 502/324; 502/325; 502/328; 502/332
[58] Field of Search ............... 502/260, 325, 324, 328, 502/332

[56] References Cited

U.S. PATENT DOCUMENTS

| 2,166,183 | 7/1939 | Signaigo | 502/325 X |
| 3,752,774 | 8/1973 | Stiles | 502/325 X |
| 3,758,584 | 9/1973 | Bivens et al. | 502/325 X |
| 4,203,870 | 5/1980 | Nielsen | 502/325 X |
| 4,439,544 | 3/1984 | Carter et al. | 502/260 X |
| 4,598,058 | 7/1986 | Frank et al. | 502/243 X |
| 4,604,275 | 8/1986 | Murib | 502/332 X |

FOREIGN PATENT DOCUMENTS 152652 8/1985 European Pat. Off. .

Primary Examiner—W. J. Shine
Attorney, Agent, or Firm—Jordan B. Bierman

[57] ABSTRACT

A process for the preparation of cobalt catalysts wherein an aqueous solution of a cobalt salt is reacted with a water soluble alkali metal carbonate in the first stage. Thereafter, the mass which has been precipitated is reduced with hydrogen at a temperature between 200° and 300° C to form the catalyst. In a preferred form of the invention, the raw catalyst is subjected to treatment with nitrogen gas containing a small amount of oxygen, whereby the catalyst is stabilized.

29 Claims, No Drawings

PROCESS FOR THE PREPARATION OF COBALT CATALYSTS

This invention is directed to a process for the production of cobalt catalysts, especially those intended for hydrogenation. In particular, reactions wherein organic nitrogen compounds comprise the reactants or the products are particularly suited to hydrogenation by the catalysts of the invention.

BACKGROUND OF THE INVENTION

In order to carry out hydrogenation reactions, it is common to use catalysts based upon cobalt and/or nickel. In particular, such catalysts are used in the conversion of nitriles (including dinitriles) to corresponding amines. Primary amines are formed by reductive amination wherein aldehydes or ketones and ammonia are hydrogenated in the presence of such cobalt or nickel catalysts. It is known to use Raney cobalt or nickel for such reactions.

In particular, such compounds as diethylaminoacetonitrile undergo this reaction in the presence of Raney nickel to form the corresponding diamine. However, the yield is only 37% which is too low for a commercially viable process. This reaction and yield is set forth in Winans and Adkins (Am. Soc. 55, 4167 (1933)). However, even this yield has been found not readily reproducible (cf. Houben-Weyl 11/1, page 563).

GB-PS 745 684 describes a process for the production of N,N-dialkylaminoethylamine by catalytic hydrogenation of N,N-dialkylaminoacetonitrile at elevated pressures and temperatures below 110° C. Raney cobalt is used and the process, which requires liquid ammonia, produces a yield of 92%.

In general, a relatively complete description of reductive amination of carbonyl compounds etc. with Raney nickel catalysts is set forth in Houben-Weyl, Methoden der organischen Chemie, Stuttgart 1957, volume XI/1, page 602 et seq. In spite of their excellent activity, Raney nickel and cobalt catalysts have not been fully adopted in industry. One of the main reasons for this is that such catalysts are difficult to handle, can only be used in suspended form and not as fixed bed catalysts, and are relatively complicated to prepare.

BRIEF DESCRIPTION OF THE PRESENT INVENTION

Therefore, it is among the objects of the present invention to develop catalysts which are easy to prepare, usable as fixed bed and fluid catalysts, and have substantially the same high activity level as the known Raney cobalt catalysts.

The present invention is a process for the preparation of cobalt catalysts which comprises precipitation of cobalt compounds from an aqueous solution of a cobalt salt. It is carried out in two stages, the first being a reaction with a water soluble alkali metal carbonate which causes the initial precipitation. Thereafter, the catalysts may be filtered, washed, and shaped into a desired mass.

The second stage comprises reduction of the precipitated mass using hydrogen between 200° and 300° C. which results in the formation of the catalysts. It has been found particularly advantageous to carry out the precipitation by adding the carbonate in the form of a water solution thereof and to carry out the precipitation at 20° C.

DETAILED DESCRIPTION OF THE INVENTION

In particular, it has been found advantageous to include certain additives to the catalyst. In a preferred embodiment, the catalysts contains 0.25% to 15% by weight, based on the total mass of catalyst in its anhydrous state and prior to the reduction step. These additives are in the form of oxides, hydroxides, or oxide hydrates. They can be used alone or in combinations thereof. The preferred amount is 1% to 8%, especially 2% to 5%. These additives may be present as oxides, hydroxides, and especially as oxide hydrates in both the unreduced mass and the reduced catalyst.

While the theory of the activity of the additives is not clear, it appears that they tend to stabilize the structure of the catalyst, especially the surface thereof, against sintering at high temperatures. In addition, the mechanical stability of shapes formed from the catalyst is also increased.

In preparation of the cobalt catalysts of the present invention, a mass which is substantially cobalt carbonate is precipitated out of the aqueous solution of a cobalt salt by reaction with alkali metal carbonate. As used herein, cobalt carbonate should be understood to include not only the compound itself, but also basic carbonates and other products of the reaction between the salt and the alkali metal carbonate under the reaction conditions set forth. Among the suitable cobalt salts are the nitrate, chloride, sulfate, and acetate. The preferred alkali metal is sodium or potassium.

It has been found suitable to provide 25 to 150 g/liter of the cobalt salt and the alkali metal carbonate. In a preferred form of the invention, an aqueous solution of the cobalt salt and a water solution of the alkali metal carbonate (in the concentrations set forth) are mixed together, preferably at 20° C. to 95° C., to cause the desired precipitate. While the reaction takes place basically on an equimolar basis, it has been found desirable to have an excess of alkali carbonate present. More specifically, 1.1 to 1.5, particularly 1.2 to 1.3, mols of carbonate to 1 mol of cobalt salt has been found suitable.

The introduction of the additives is not particularly critical. They can be suspended in the cobalt salt solution, or in the alkali metal carbonate solution. They can also be added to the salt solution before precipitation and thereby are precipitated out with the cobalt carbonate itself. It is even possible to precipitate the cobalt carbonate separately and to thereafter precipitate the additive onto the carbonate.

The silicon additives may be produced, for example, by acidifying a sodium silicate solution or by hydrolysis of a silicon halide. The compounds of manganese are prepared by reacting manganese (II) compound such as the nitrate or chloride with alkali metal hydroxide or alkali metal carbonate. A similar procedure is used for zirconium. For example, $Zr(NO_3)_4 \cdot 5H_2O$ or $ZrOCl_2 \cdot 8H_2O$ can be reacted with ammonia, alkali metal hydroxide or alkali metal carbonate. The aluminum additive is prepared from the nitrate with ammonia or alkali metal carbonate. The magnesium additive is also obtained from the nitrate but by the use of alkali metal hydroxide or alkali metal carbonate. These precipitations to form the oxygen containing additives takes place at 70° to 95° C., preferably at 80° to 90° C.

It is a feature of the present invention that the reduction step take place from 200° C. to 300° C. The preferred range is 220° C. to 280° C. It has been found especially desirable to carry out the reduction in at least three stages at temperatures which increase with each stage. Advantageously, the first stage is carried out at 220° C. to 250° C., the second stage at 245° to 260° C., and the third stage from 255° to 280° C. The preferable ranges are 230° to 240° C. for the first stage, 250° to 255° C. for the second stage, and 260° to 270° C. for the third stage.

The range of reaction times will vary somewhat depending upon the temperatures used. In the case of the broader ranges, the first stage will take 1 to 4 hours, the second stage will take 1 to 5 hours, and the third stage will also take 1 to 5 hours. If the preferred temperature ranges are used, each of the three stages will take from 2 to 3 hours.

It has also been found useful to provide two or more steps within some or all of the three stages set forth above. For example, the first stage can be carried out in two steps wherein the first step is at 220° to 230° C. for 1 hour and the second step at 230° to 240° C. for 1.5 hours.

The hydrogen is advantageously passed over the mass to be reduced at a space velocity of 200 to 2,000 liters thereof per liter of mass per hour. The preferred range is 300 to 1,000 and the most preferred range is 400 to 700.

The catalysts which has been reduced is spontaneously inflammable in air. This, of course, presents a handling problem. It is a feature of the present invention that the reduced catalyst is contacted by a stream of nitrogen containing some oxygen, in particular, about 0.5% to about 1.0% by volume. This treatment causes oxidation of the surface of the catalyst which stabilizes it in air and prevents spontaneous inflammability up to about 80° C.

The catalysts of the present invention have a BET surface of 10 to 80 m$^2$/g, preferably 40 to 60 m$^2$/g. The pour volume is 0.1 to 0.6 ml/g, preferably 0.3 to 0.4 ml/g. These catalysts can be formed into various shapes, such as strands or, in particular, tablets. It has been found that these exhibit low abrasion even under high loads. While the catalyst can be suspended in a solvent, it has been found of a special advantage to use them as fixed-bed catalysts.

The following examples are intended to illustrate the invention, but are not to be construed as limitative.

EXAMPLE 1

Preparation of a Cobalt Catalyst without Additives

A solution, heated to 95° C., of 1852 g of Co(NO$_3$)$_2$.6H$_2$O (containing about 375 g Co) in 7.5 liters of deionized water is poured into a solution, heated to 90° C., of 800 g of Na$_2$CO$_3$ in 7.5 liters of deionized water over a period of 2 minutes with vigorous stirring. The precipitate suspension exhibits a pH value of 8.2 to 8.4. The product is filtered off and thoroughly rinsed with about 90 liters of condensate water (temperature: 70° C.) until the conductivity of the rinsing water is ≦100 μS. The preliminary product which is still moist is suspended again, then spray-dried or extruded, and dried for 12 hours in an air stream at temperatures increasing from 50° to 75° C. The extrudate mass exhibits the following characteristics:

| | |
|---|---|
| bulk density: | 600 to 770 g/l |
| Co content: | about 53.5% by weight |
| CO$_3$ content: | 23.5% by weight |
| residual alkali metal content: | about 0.06 to 0.2% by weight of Na$_2$O |
| residual moisture: | ≦10% by weight |

In the reduction process, 200 liters of H$_2$/hour are passed over 0.5 liters of the extruded and dried catalyst mass in a tubular reactor (diameter: 50 mm) at 240° C. over a period of 2 hours. Then the temperature is raised to 250° C. and reduction is continued for another 2 hours with 200 liters of H$_2$/hour and completed by treating the catalyst for another 2 hours with 200 liters of H$_2$/hour at 260° C.

For better handling, the reduced catalyst is first treated for 4 hours at ambient temperature and then for 2 hours at 70° C. with an N$_2$ stream containing 0.7% by volume of O$_2$, at the rate of 1000 liters of N$_2$ per liter of catalyst per hour. The catalyst obtained by this process can then be ground to powder or pressed into tablet form.

EXAMPLE 2

Preparation of a Cobalt Catalyst with Additives

A solution, heated to 95° C., of 1852 g of Co(NO$_3$)$_2$.6H$_2$O (containing about 375 g of Co) and 85.73 g of Mn(NO$_3$)$_2$.4H$_2$O in 7.5 liters of deionized water is steadily poured into a solution, heated to 90° C., of 840 g of Na$_2$CO$_3$ in 7.5 liters of deionized water over a period of 2 minutes with vigorous stirring. A suspension of cobalt and manganese carbonate in water with a pH value of 8.2 to 8.4 is formed. The precipitation product is filtered off and washed thoroughly with roughly 90 liters of 70° C. hot condensate water so that the conductivity of the rinsing water is less than 100 μS on completion of the washing process.

The still moist preliminary product is again suspended in deionised water, then spray-dried or extruded, and dried for 12 hours in an air stream at a temperature increasing from 50° to 75° C. The extrudate mass has the following characteristics:

| | |
|---|---|
| bulk density: | 600 to 730 g/l |
| Co content: | about 52% by weight |
| MnO$_2$ content: | 4.1% by weight |
| CO$_3$ content: | about 22.5% by weight |
| residual alkali metal content: | about 0.08 to 0.3% by weight of Na$_2$O |
| residual moisture: | ≦10% by weight |

The reduction of the catalyst takes place as described in Example 1.

EXAMPLE 3

Hydrogenation of Diethylaminoacetonitrile 1.8 liters of the cobalt catalyst of Example 1 is arranged in the form of tablets 6 mm in diameter as a fixed bed catalyst in a heatable 3 m long double-jacket tube with an inside diameter of 28 mm. The temperature is raised to 70° C. and hydrogen is fed in continuously at a pressure of 8 MPa at the bottom of the reaction tube together with 600 ml per hour of a solution of diethylaminoacetonitrile in cyclohexane (15% by weight of nitrile based on the solution) via a piston pump.

The product discharging at the reactor head does not contain any diethylaminoacetonitrile. In addition to 86.5% of solvent, 11% of diethylaminoethylamine are detected by gas chromatography.

EXAMPLE 4

Hydrogenation of Diethylaminoacetonitrile

In the reactor of Example 3 and using 1.8 liters of the catalyst of Example 2 at 60° C. and a $H_2$ pressure of 8 MPa, diethylaminoacetonitrile in the form of a 30% by weight solution (based on the solution) is reacted to form cyclohexane. At the same time, 2.5 mols of $NH_3$ per mol of nitrile are fed into the reactor and the throughput increased to 900 ml/h. The diethylaminoacetonitrile is completely reacted. The gas chromatography analysis shows the reaction product to contain 73.2% cyclohexane and 25.1% diethylaminoethylamine.

EXAMPLE 5

Hydrogenation of Diethylaminoacetonitrile

Undiluted diethylaminoacetonitrile is reacted in the reactor of Example 3 at 50° C. and at a $H_2$ pressure of 8 MPa. 2.5 mols of $NH_3$ are fed into the reactor per mol of nitrile, and the throughput is set to 180 ml/h, V/Vh (space velocity)=0.1. The nitrile is completely reacted, the gas chromatography analysis shows the reaction product to contain 89.7% diethylaminoethylamine, the reaminder being cleavage products. The reaction product is worked up in a column with 24 theoretical plates. Diethylaminoethylamine of more than 99% purity is recovered.

I claim:

1. A process for the preparation of carrier-free cobalt catalysts consisting essentially of precipitation, from an aqueous solution of a cobalt salt, of a substance by reaction with a water-soluble alkali metal carbonate to form a mass and
    reduction of said mass with hydrogen to form said catalyst, said reduction being conducted in at least three stages, a first stage at 220° C. to 250° C., a second stage at 245° C. to 260° C., and a third stage at 255° C. to 280° C.

2. The process of claim 1 wherein said alkali metal carbonate is added to said aqueous solution in the form of a water solution thereof.

3. The process of claim 1 wherein said precipitation takes place at 20° to 95° C.

4. The process of claim 1 wherein at least one additive taken from the class consisting of $SiO_2$, $MnO_2$, $ZrO_2$, $Al_2O_3$, or MgO is present in the form of an oxide, hydroxide, and/or oxide hydrate.

5. The process of claim 4 wherein said additive is present in an amount of 0.25% to 15% based on said mass in an anhydrous state.

6. The process of claim 4 wherein said additive is present in an amount of 1% to 8% by weight based on said mass in an anhydrous state.

7. The process of claim 5 wherein said amount is 2% to 5%.

8. The process of claim 4 wherein said additive is in the form of said oxide hydrate.

9. The process of claim 1 wherein said salt is a nitrate, chloride, sulfate, or acetate.

10. The process of claim 1 wherein said alkali metal is sodium or potassium.

11. The process of claim 1 wherein there is 25 to 150 g/liter of cobalt salt and 25 to 150 g/liter of said alkali metal carbonate in said aqueous solution.

12. The process of claim 2 wherein there is 25 to 150 g/liter of cobalt in said aqueous solution and 25 to 150 g/liter of said alkali metal carbonate in said water solution.

13. The process of claim 11 wherein there is 1.1 to 1.5 mols of said alkali carbonate per mol of said cobalt salt.

14. The process of claim 3 wherein there is 1.2 to 1.3 mols of said alkali carbonate per mol of said cobalt salt.

15. The process of claim 4 wherein said additive is suspended in said aqueous solution before said precipitation.

16. The process of claim 4 wherein said alkali carbonate is added to said aqueous solution as a water solution thereof, said additive being suspended in said water solution.

17. The process of claim 4 wherein said additive is precipitated on said mass.

18. The process of claim 1 wherein said hydrogen is passed over said mass at a space velocity of 200 to 2000 liters per liter of said mass per hour.

19. The process of claim 18 wherein said space velocity is 300 to 1000 liters per liter of said mass per hour.

20. The process of claim 19 wherein said space velocity is 400 to 700 liters per liter of said mass per hour.

21. The process of claim 1 wherein said first stage is at 230° to 240° C., said second stage is at 250° to 255° C., and said third stage is at 260° to 270° C.

22. The process of claim 1 wherein said first stage is 1 to 4 hours, said second stage is 1 to 5 hours, and said third stage is 1 to 5 hours.

23. The process of claim 21 wherein said first stage is 2 to 3 hours, said second stage is 2 to 3 hours, and said third stage is 2 to 3 hours.

24. The process of claim 1 wherein at least one of said first, second, and third stages is carried out in a plurality of steps.

25. The process of claim 1 wherein a stream of nitrogen containing oxygen is passed over said catalyst whereby a surface of said catalyst is oxidized.

26. The process of claim 25 wherein said nitrogen contains about 0.5% to 1.0% oxygen by volume.

27. A catalyst which is the product of the process of claim 1.

28. The catalyst which is the product of the process of claim 4.

29. The catalyst which is the product of the process of claim 24.

* * * * *